US012616402B2

(12) United States Patent
Foley et al.

(10) Patent No.: US 12,616,402 B2
(45) Date of Patent: **\*May 5, 2026**

(54) UNSHIELDED PULSED PUMP MAGNETOMETERS FOR BIOMAGNETIC MEASUREMENTS

(71) Applicant: Twinleaf LLC, Plainsboro, NJ (US)

(72) Inventors: Elizabeth L. Foley, Plainsboro, NJ (US); Thomas W. Kornack, Plainsboro, NJ (US); Lucia A. Rathbun, Princeton, NJ (US); David H Newby, Pennington, NJ (US); Nancy G. Ford, Bordentown, NJ (US)

(73) Assignee: TWINLEAF LLC, Plainsboro, NJ (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/631,976

(22) Filed: Apr. 10, 2024

(65) Prior Publication Data

US 2024/0268739 A1 Aug. 15, 2024

Related U.S. Application Data

(63) Continuation of application No. 18/389,433, filed on Nov. 14, 2023.

(Continued)

(51) Int. Cl.
*A61B 5/243* (2021.01)
*A61B 5/242* (2021.01)
(Continued)

(52) U.S. Cl.
CPC .............. *A61B 5/243* (2021.01); *A61B 5/242* (2021.01); *A61B 5/245* (2021.01); *A61B 5/248* (2021.01);
(Continued)

(58) Field of Classification Search
CPC ......... A61B 5/243; A61B 5/242; A61B 5/245; A61B 5/248; A61B 2562/0223; A61B 2562/046; G01R 33/032
See application file for complete search history.

(56) References Cited

U.S. PATENT DOCUMENTS 4,793,355 A 12/1988 Crum et al.
7,038,450 B2 5/2006 Romalis et al.
(Continued)

FOREIGN PATENT DOCUMENTS

WO WO-2020120924 A1 \* 6/2020

OTHER PUBLICATIONS

Jaufenthaler, Aaron, et al. "Pulsed optically pumped magnetometers: Addressing dead time and bandwidth for the unshielded magnetorelaxometry of magnetic nanoparticles." Sensors 21.4 (2021): 1212. (Year: 2021).\*

(Continued)

*Primary Examiner* — Sean D Mattson
(74) *Attorney, Agent, or Firm* — Myers Wolin, LLC

(57) ABSTRACT

The pulsed pump magnetometer (PPM) is a new type of magnetometer with much higher dynamic range, linearity, and sensitivity than all other types of magnetometers. These features allow more faithful subtracting and cancelling sources of magnetic noise, enabling high quality biomagnetic measurements. Using an array of PPM sensors enables high quality measurements of biomagnetic signals even in magnetically noisy, real-world conditions like medical offices. Arrays of PPM sensors improve upon pulsed magnetic gradiometers in providing higher sensitivity per sensor and superior noise rejection through noise decorrelation and covariance modeling. Arrays of PPM sensors enable localization and imaging of biomagnetic sources.

20 Claims, 9 Drawing Sheets

820 Probe
810 Pulsed Pump
830 Alkali vapor cell
Coil 840
850 Detector

Related U.S. Application Data

(60) Provisional application No. 63/425,453, filed on Nov. 15, 2022, provisional application No. 63/425,446, filed on Nov. 15, 2022.

(51) Int. Cl.

| | |
|---|---|
| *A61B 5/245* | (2021.01) |
| *A61B 5/248* | (2021.01) |
| *G01R 33/032* | (2006.01) |
| *G01R 33/26* | (2006.01) |

(52) U.S. Cl.
CPC ........... *G01R 33/032* (2013.01); *G01R 33/26* (2013.01); *A61B 2562/0223* (2013.01); *A61B 2562/046* (2013.01)

(56) References Cited

U.S. PATENT DOCUMENTS

| | | | |
|---|---|---|---|
| 7,145,333 | B2 | 12/2006 | Romalis et al. |
| 7,521,928 | B2 | 4/2009 | Romalis et al. |
| 9,575,144 | B2 | 2/2017 | Kornack et al. |
| 9,638,768 | B2 | 5/2017 | Foley et al. |
| 9,915,711 | B2 | 3/2018 | Kornack et al. |
| 10,107,877 | B2 | 10/2018 | Foley et al. |
| 10,345,548 | B2 | 7/2019 | Dural et al. |
| 10,466,317 | B2 | 11/2019 | Sheng et al. |
| 10,852,371 | B2 | 12/2020 | Romalis et al. |
| 10,955,495 | B2 | 3/2021 | Foley et al. |
| 2009/0149736 | A1* | 6/2009 | Skidmore .............. A61B 5/246 600/421 |
| 2013/0121927 | A1* | 5/2013 | Flynn .................... A61B 5/418 424/9.34 |
| 2019/0125205 | A1* | 5/2019 | Kawabata .............. A61B 5/242 |
| 2019/0391213 | A1* | 12/2019 | Alford .............. G01R 33/0094 |
| 2020/0334559 | A1* | 10/2020 | Anderson .............. G06N 20/00 |
| 2022/0091200 | A1* | 3/2022 | Gerginov ............... G01R 33/26 |
| 2022/0409156 | A1* | 12/2022 | Miyano .................. A61B 5/248 |
| 2023/0074561 | A1* | 3/2023 | Park ....................... A61B 5/065 |
| 2023/0204688 | A1 | 6/2023 | Setegn et al. |
| 2024/0197227 | A1* | 6/2024 | Foley .................... A61B 5/245 |

OTHER PUBLICATIONS

Beadle et al., "Assessing heart disease using a novel magnetocardiography device," Biomedical Physics & Engineering Express, 2021, pp. 1-9, vol. 7, IOP Publishing.

Alday et al., "Comparison of Electric- and Magnetic-Cardiograms Produced by Myocardial Ischemia in Models of the Human Ventricle and Torso," PLoS ONE, Aug. 24, 2016, pp. 1-11, vol. 11, No. 8.

Yin et al., "Electrogastrography: Methodology, Validation and Applicants, "Journal of Neurogastroenterology and Motility, Jan. 2013, pp. 1-13, vol. 19, No. 1, the Korean Society of Neurogastroenterology and Motility.

Feys et al. "On-Scalp Optically Pumped Magnetometers versus Cryogenic Magnetoencephalography for Diagnostic Evaluation of Epilepsy in School-aged Children," Radiology, 2022, pp. 1-6, vol. 00, No. 0-2022, RSNA.

Akaza et al., "Noninvasive measurement of sensory action currents in the cervical cord by magnetospinography," Clinical Neurophysiology, 2020, pp. 1-43, Elsevier B.V. on behalf of International Federation of Clinical Neurophysiology.

Jaufenthaler et al., "Pulsed Optically Pumped Magnetometers: Addressing Dead Time and Bandwidth for the Unshielded Magnetorelaxometry of Magnetic Nanoparticles," Sensors, Feb. 9, 2021, pp. 1-19, vol. 21, No. 1212, MDPI.

Yang et al., "A new wearable multichannel magnetocardiogram system with a SERF atomic magnetometer array," Scientific Reports, 2021, pp. 1-11, vol. 11, No. 5564, Natureportfolio.

* cited by examiner

310

315

415

410

510

UNSHIELDED PULSED PUMP MAGNETOMETERS FOR BIOMAGNETIC MEASUREMENTS

CROSS REFERENCE TO RELATED APPLICATIONS

This application is a continuation of U.S. Non-provisional patent application Ser. No. 18/389,433 filed on Nov. 14, 2023, which claims the benefit of U.S. Provisional Patent Application No. 63/425,453 filed on Nov. 15, 2022, and U.S. Provisional Patent Application No. 63/425,446 filed on Nov. 15, 2022. The contents of U.S. Non-provisional patent application Ser. No. 18/389,433, U.S. Provisional Patent Application No. 63/425,453 and U.S. Provisional Patent Application No. 63/425,446 are hereby incorporated by reference.

TECHNICAL FIELD

The present disclosure generally relates to magnetic field and magnetic field gradient measurements, and more particularly to magnetic field measurements of biological sources.

BACKGROUND

Biomagnetic measurements are magnetic measurements of biological activity, including but not limited to the heart (magnetocardiography), brain (magnetoencephalography), nerves and muscles (magnetomyography), and digestion (magnetogastrography).

Various types of magnetometer have been used to perform biomagnetic measurements, such as superconducting quantum interference device (SQUID) sensors, and zero field/SERF optically pumped magnetometers (OPM). High quality measurements are obtained only with extensive magnetic shielding and/or magnetic environment conditioning.

Measurements are significantly degraded by magnetic noise when magnetometers are operated without shielding. Typical magnetic noise is a combination of geomagnetic sources such as the dynamics of the ionosphere and the solar wind and human sources such a power lines, electronics, and movement of magnetic objects. Pulsed pump gradiometers have been demonstrated to reject magnetic noise by subtracting the magnetic field measurement at two points.

SUMMARY

The pulsed pump magnetometer (PPM) is a new type of magnetometer with much higher dynamic range, linearity, and sensitivity than all other types of magnetometers. These features allow it to more faithfully subtract and cancel sources of magnetic noise, enabling high quality biomagnetic measurements. Using an array of PPM sensors enables high quality measurements of biomagnetic signals even in magnetically noisy, real-world conditions like medical offices. Arrays of PPM sensors improve upon pulsed magnetic gradiometers in providing higher sensitivity per sensor and superior noise rejection through noise decorrelation and covariance modeling. Arrays of PPM sensors enable localization and imaging of biomagnetic sources.

An embodiment of the present disclosure provides a system for measuring biomagnetic signals a biological subject in an unshielded environment, including: a pulsed pump magnetometer (PPM) arranged at a desired location over the biological subject; a controller configured to operate the PPM to detect a biomagnetic signal from the biological subject over a period of time; and a processor configured to process the detected biomagnetic signal to generate a result indicative a characteristic or condition associated with of the biological subject; wherein the PPM measures the projection of the biomagnetic signal on the background magnetic field in the unshielded measurement environment; wherein the PPM includes at least one atomic vapor cell with at least one pulsed pump laser and at least one probe laser which is pulsed or operated continuously and a control unit configured to convert the detected light signals from the probe to total magnetic field measurements and the PPM is configured to operate in the range of background magnetic fields from less than 1 µT to more than 100 µT.

An embodiment of the present disclosure provides a method of measuring biomagnetic signals in an unshielded environment using a pulsed pump magnetometer (PPM), including: arranging one or more PPM at a desired location over a biological subject; operating the one or more PPM to detect a biomagnetic signal from the biological subject over a period of time; processing the detected biomagnetic signal to generate a result indicative a characteristic or condition associated with of the biological subject; wherein the PPM measures the projection of the biomagnetic signal on the background magnetic field in the unshielded measurement environment; wherein each PPM includes at least one atomic vapor cell with at least one pulsed pump laser and at least one probe laser which is pulsed or operated continuously and a control unit configured to convert the detected light signals from the probe to total magnetic field measurements and the PPM is configured to operate in the range of background magnetic fields from less than 1 µT to more than 100 µT.

DETAILED DESCRIPTION

Figure 1:
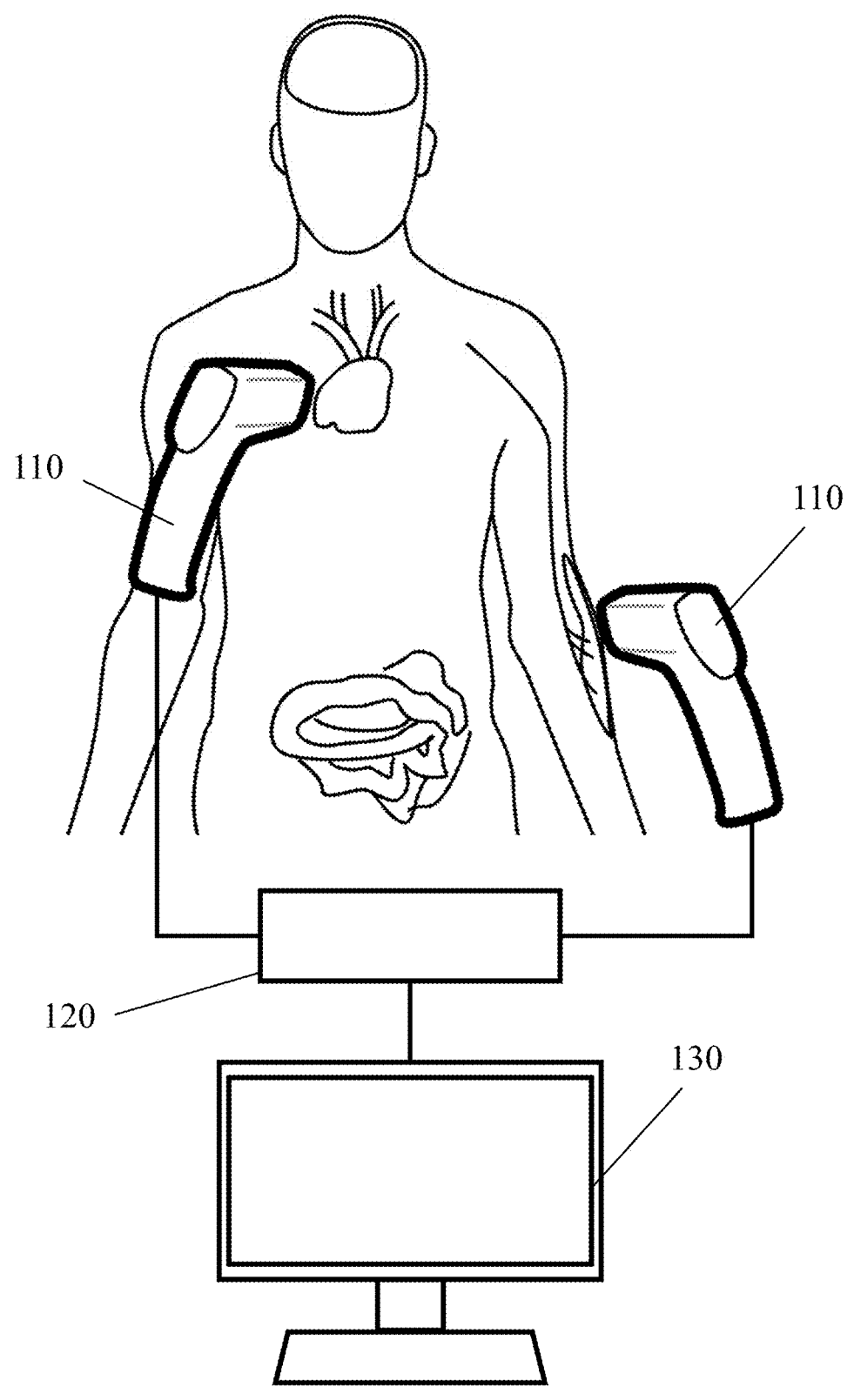
FIG. 1 illustrates the measurement of biomagnetic signals using sensors in an unshielded environment according to one embodiment.

The description of illustrative embodiments according to principles of the present disclosure is intended to be read in connection with the accompanying drawings, which are to be considered part of the entire written description. In the description of embodiments of the disclosure herein, any reference to direction or orientation is merely intended for convenience of description and is not intended in any way to limit the scope of the present disclosure. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the disclosure are illustrated by reference to the exemplified embodiments. Accordingly, the disclosure expressly should not be limited to such exemplary embodiments illustrating some possible non-limiting combination of features that may exist alone or in other combinations of features; the scope of the disclosure being defined by the claims appended hereto.

This disclosure describes the best mode or modes of practicing the disclosure as presently contemplated. This description is not intended to be understood in a limiting sense, but provides an example presented solely for illustrative purposes by reference to the accompanying drawings to advise one of ordinary skill in the art of the advantages and construction of the certain embodiments. In the various views of the drawings, like reference characters designate like or similar parts.

It is important to note that the embodiments disclosed are only examples of the many advantageous uses of the innovative teachings herein. In general, statements made in the specification of the present application do not necessarily limit any of the various claimed disclosures. Moreover, some statements may apply to some inventive features but not to others. In general, unless otherwise indicated, singular elements may be in plural and vice versa with no loss of generality.

Figure 8:
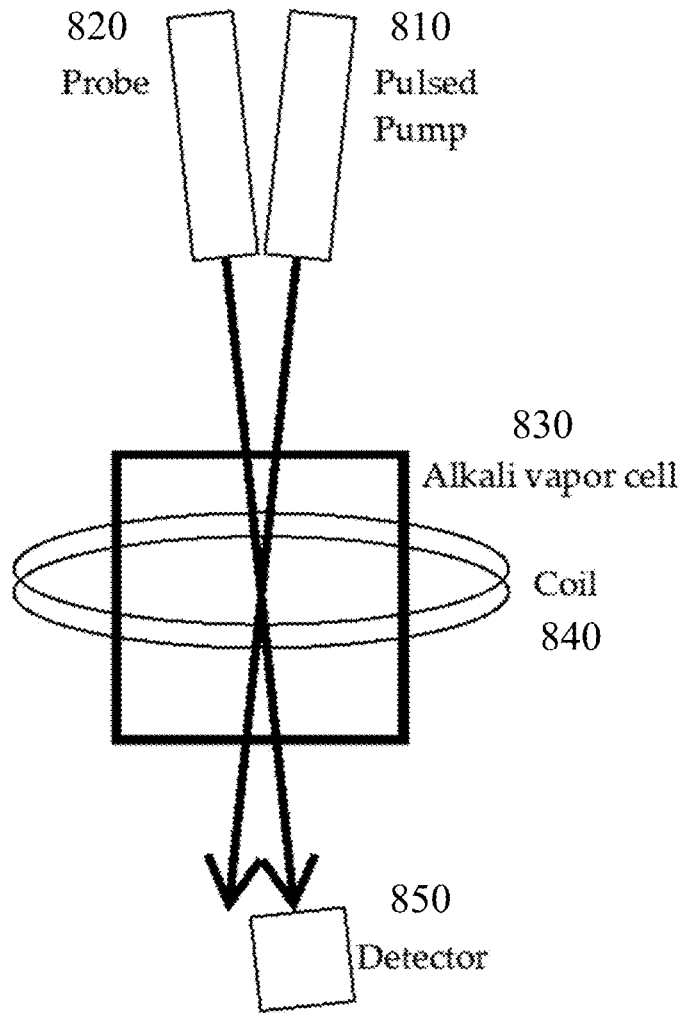
FIG. 8 is a pulsed pump magnetometer with field coil to aid pumping according to one embodiment.

FIG. 8 shows a pulsed pump magnetometer with an optional field coil 840 that generates a magnetic field parallel to the pump axis to aid pumping according to an embodiment. A pulsed pump laser 810 is configured to generate light pulses into the atomic vapor cell 830 along a pump axis. In one embodiment, the atomic vapor includes an alkali metal; and in other embodiments, suitable atoms are used, such as metastable Helium, etc. The probe laser 820 is configured to generate a probe light into the atomic vapor cell. The detector 850 is configured to detect a signal from the atomic vapor cell. It is desirable to have the coil turn off quickly; faster than the Larmor precession period, so a small coil with low inductance L is preferred to minimize L/R time. Adding extra resistance to the coil circuit as needed can speed the shutoff time. In one embodiment, the coil and laser are placed in series to simplify the circuit. In one embodiment, the laser is shut off before the coil is shut off to allow time for the atomic state to settle. The magnetic field is designed to have a gradient so that atomic spin excitation is rapidly decohered according to one embodiment.

In one embodiment, a mirror or prism is used to reflect light in the sensor. The mirror is coated with a reflective coating that is designed to impart zero relative phase shift between S and P polarization states, and the reflected light does not alter its polarization state.

In one embodiment, a non-polarizing beam splitter is used to combine light from the pump laser and the probe laser. The beam splitter is coated with a partially reflective coating that is designed to impart zero relative phase shift between S and P polarization states, and the light does not change its polarization state. Circularly polarized light and linearly polarized light with any angle remain in the same polarization state.

Figure 9:
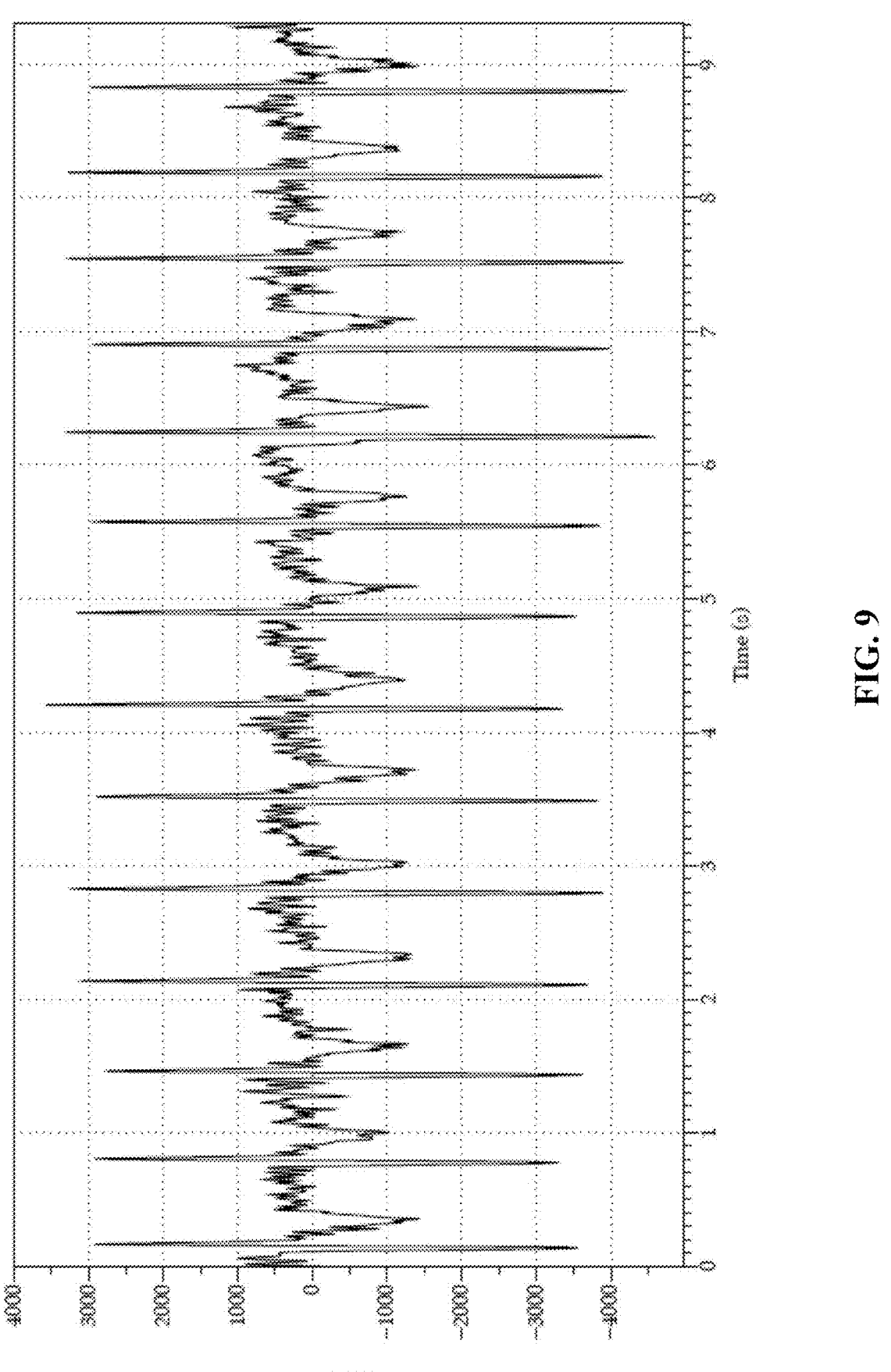
FIG. 9 shows the measurement results of using an unshielded array of 2 sensors over the heart according to one embodiment.

An array of PPM sensors discussed above can be used to record small magnetic signals from local sources. The array size and geometry can be configured to measure virtually any part of the human body. With two sensors, simple and portable systems can be configured to make high quality, non-contact measurements of the human heart and other biomagnetic sources. With more sensors in array, the sensors can locate biomagnetic sources and form magnetic images of the magnetic field. FIG. 1 shows a measurement of biomagnetic signals using sensors in an unshielded environment according to an embodiment. One or more sensors 110 are used to detect biomagnetic signals from a biological subject 140. The PPM measures the projection of the biomagnetic signal on the background magnetic field in the unshielded measurement environment. Each sensor includes one or more PPMs that are driven by a controller 120, and signals detected by the sensors 110 are sent to a processor 130 which is configured to process and analyze the data and information extracted from the signals. The processor 130 contains processing algorithms specific to the part of the human body being measured to interpret the data and generate results associated with a characteristic or condition of the body part. FIG. 9 shows the measurement results of using an unshielded array of two sensors over the heart according to one embodiment. As can been seen from FIG. 9, high quality signals are detected even in an unshielded environment.

In larger 2D or 3D arrays of sensors, the additional measurements can provide clearer and more accurate source localization as well as superior noise modeling and rejection. The larger number of measurement points are used to model noise sources by analyzing the covariance of the noise and separate the local signals of interest from more distant noise signals.

Figure 3:
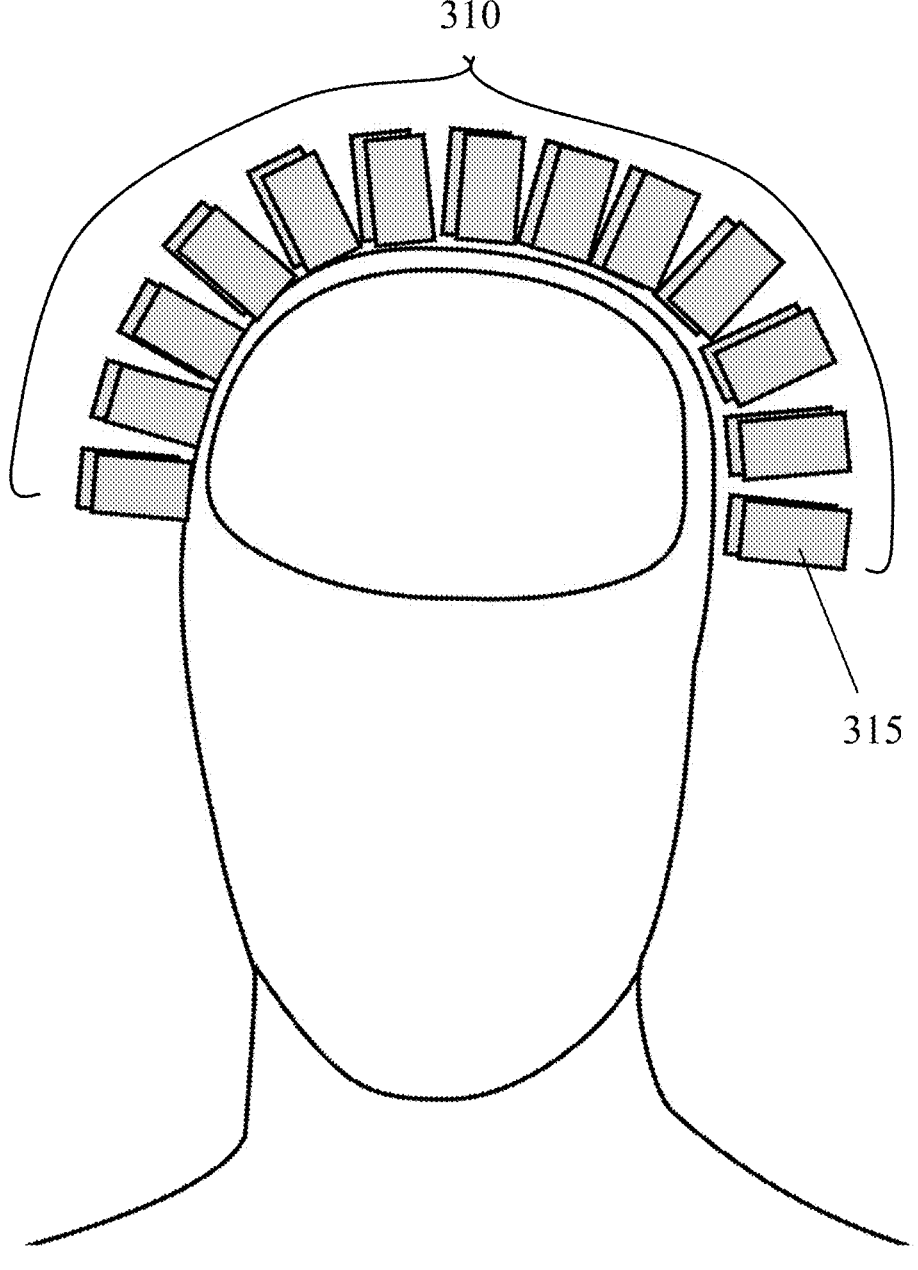
FIG. 3 shows an unshielded array of sensors for magnetoencephalography (MEG) arranged over the scalp according to one embodiment.

An MEG system can be constructed from an array of PPM sensors distributed around the scalp, similar to many other previous MEG systems, but now the system can be used entirely without a magnetic shield. As total field magnetometers, the PPM sensors are sensitive to the vector component of the signal parallel to the background field. Other vector components can be obtained by changing the orientation of the background field or the orientation of the subject. FIG. 3 shows an unshielded array of sensors for magnetoencephalography (MEG) according to an embodiment. In one embodiment, the magnetoencephalography device includes: a device configured to fit on or near the head of a subject, the device 310 having a plurality of PPM 315 attached to respective desired locations on the device, the plurality of PPM being configured to detect neuromagnetic signals from the subject over a period of time; a control unit to operate the PPM sensors; and a processor configured to process the detected neuromagnetic signals to generate at least one neural activity image; wherein PPM array will detect the magnetic fields generated by the brain activity. The PPM measures the total magnetic field so in a background field of significantly greater magnitude than the brain-generated fields, the PPM measurement will be dominated by the projection of the brain-generated field onto the background field. The background field is pre-existing or applied in conjunction with the PPM system. The head and/or background field is reoriented to measure different components of the fields generated by the brain. The PPM array consists of a set of paired PPMs as two-point gradiometers, or consists of a set of multiple independent PPMs operated independently and subject to post-processing as higher order multiple gradiometers; wherein the PPM includes a pulsed polarization means (e.g., polarization coil), a probing means, a sensing volume, and a detector. The PPM is configured to operate in the range of 0.1 μT to 100 μT.

In one embodiment, a brain-controlled computer device is provided. The brain-controlled computer device includes a device configured to fit on or near the head of a subject, the device having a plurality of PPM attached to respective desired locations on the device, the plurality of PPM being configured to detect neuromagnetic signals from the subject over a period of time; a control unit to operate the PPM sensors; and a processor configured to process the detected neuromagnetic signals to identify at least one neural activity, and generate a control signal to the computer if at least one characteristic of the at least one neural activity exceeds a predetermined threshold.

Figure 2:
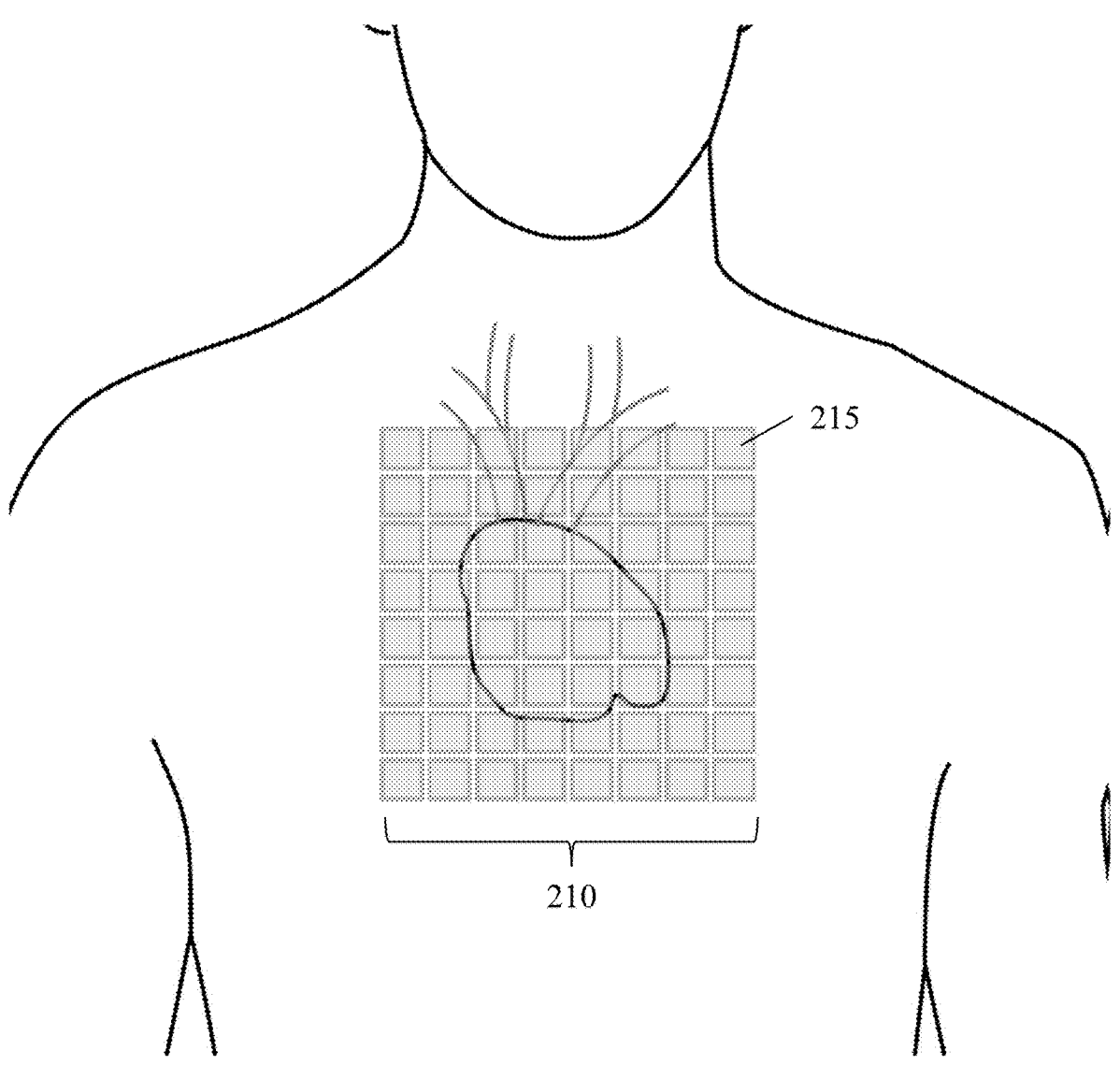
FIG. 2 shows an unshielded array of sensors for magnetocardiography (MCG) arranged over the heart according to one embodiment.

An MCG system can be constructed using an array of unshielded PPM sensors distributed in a 2D grid on the chest. The resulting 2D image of the heart can be used to diagnose a variety of heart conditions and potentially localize problems. The sensors could be built into a surface, wall, chair, or bed to make the measurements easily accessible for rapid testing and screening. The recordings can last as little as 10 seconds using as few as two sensors to obtain clear heart recordings. The heart signal can be averaged across multiple beats to suppress sources of noise. FIG. 2 shows an unshielded array of sensors for magnetocardiography (MCG). In one embodiment, a magnetocardiography device is used to make such measurement. The magnetocardiography device includes: an array 210 of PPM 215 configured to detect cardiac magnetic fields at corresponding locations of the heart of a subject over a period of time; The array consists of sets of paired sensing volumes each of which is configured as an individual gradiometer, or consists of a set of independent PPMs; and a processor configured to process the detected cardiac magnetic fields to generate at least one magnetocardiogram, and determine whether the at least one characteristic of the at least one magnetocardiogram exceeds a predetermined threshold; wherein the magnetic signals generated by the cardiac activity is detected by the PPM array; wherein the PPM includes at least one atomic vapor cell with at least one pulsed pump laser and at least one probe laser which is pulsed or operated continuously and a control unit capable of converting the detected light signals from the probe to total magnetic field measurements and the PPM is configured to operate in the range of background magnetic fields from less than 0.1 μT to more than 100 μT. The PPM or set of PPMs will measure the projection of the cardiac fields on the background magnetic field in the measurement environment. This is naturally occurring or applied. The relative orientation of the person/heart or the background field is controlled or adjusted to derive additional information.

Figure 4:
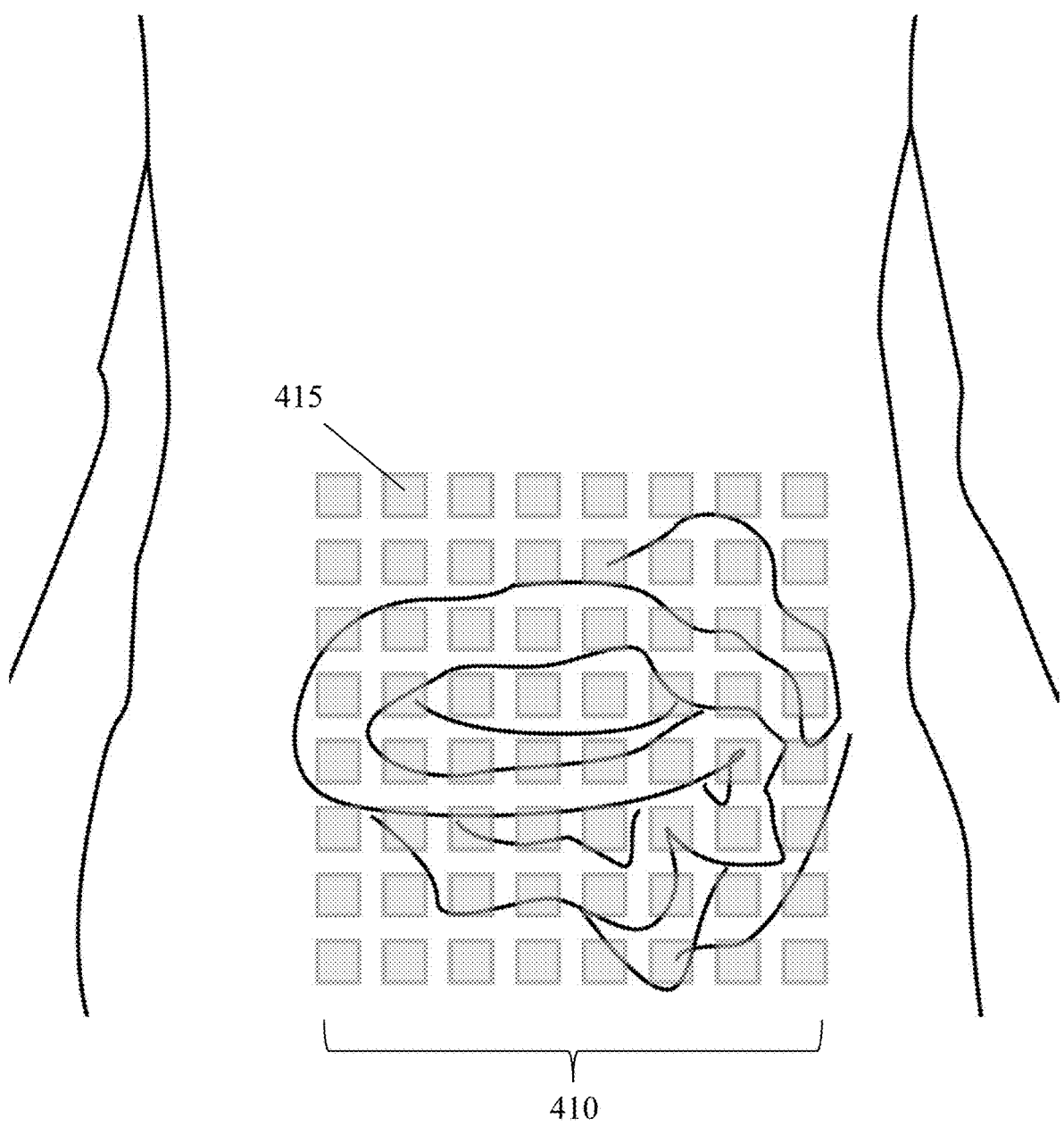
FIG. 4 shows an unshielded array of sensors for magnetogastrography (MGG) arranged over the abdomen according to one embodiment.

An MGG system can be constructed using an expanded array of unshielded PPM sensors distributed around the abdomen. MGG measurements must be recorded over long timescales to observe the slower intestinal peristalsis signals. Certain types of digestive conditions will show clearly abnormal signals, varying in both timescale, structure, and amplitude. FIG. 4 shows an unshielded array of sensors for magnetogastrography (MGG). In one embodiment, a magnetogastrography device is used to make such measurement. The magnetogastrography device includes: a vest or apparatus configured to be worn or placed over a part of the torso of a subject, the vest having an array 410 of PPM 415 configured to measure gastric magnetic fields at corresponding locations of the abdomen of the subject over a period of time; a control unit to operate the PPM sensors; and a processor configured to process the detected gastric magnetic fields to generate at least one magnetogastrogram, and determine whether at least one characteristic of the at least one magnetogastrogram exceeds a predetermined threshold; wherein the PPM has high sensitivity, high dynamic range, and high linearity that permit subtraction of environmental magnetic noise and resolution of small signals of interest. The PPM includes a pulsed polarization means, a probing means, a sensing volume, and a detector. The PPM is configured to operate in the range of 0.1 μT to 100 μT. The PPM has high sensitivity, high dynamic range, and high linearity that permit subtraction of environmental magnetic noise and resolution of small signals of interest. The torso and/or background field is reoriented to measure different components of the fields generated by the organs inside the torso.

Figure 5:
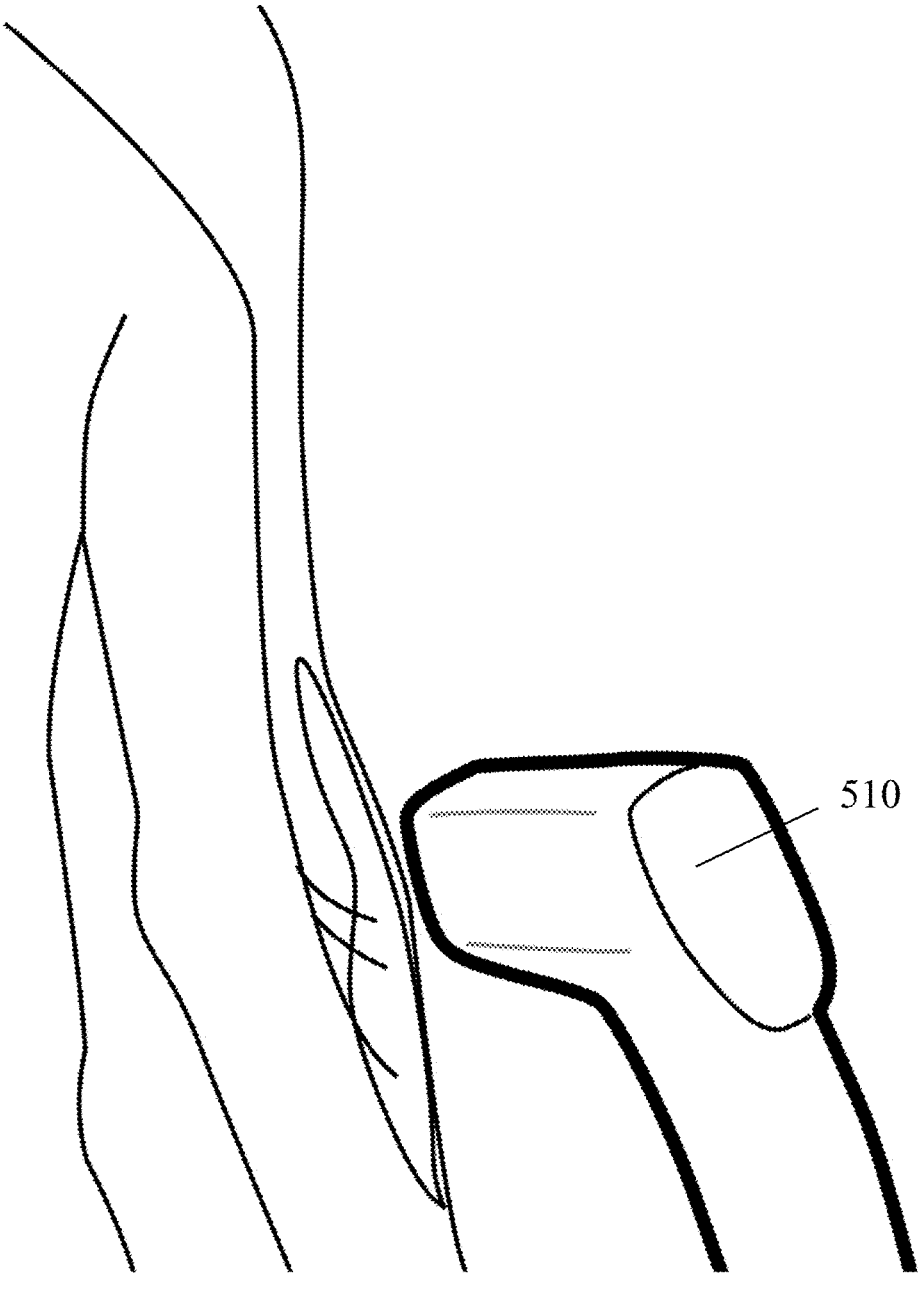
FIG. 5 shows an unshielded sensor for magnetomyography (MMS) of nerve and muscle activity around the body according to one embodiment.

A magnetomyography (MMS) system can be constructed using a set of unshielded PPM sensors. To monitor the quality of nerve connection, a repeated action or motion can be performed and the resulting nerve activity measured. Weak or abnormal nerve activity can inform diagnosis and treatment. FIG. 5 shows an unshielded sensor for magnetomyography of nerve and muscle activity around the body. In one embodiment, a magnetomyography device is used to make such measurement. The magnetomyography device includes: one or more sensors 510, or in a larger area, a vest configured to be worn over a part of the torso of a subject, the vest having an array of PPM configured to measure magnetic fields associated with sensory activities at corresponding locations of the muscles of the subject over a period of time; a control unit to operate the PPM sensors; and a processor configured to process the detected magnetic fields to generate at least one magnetomyogram, and determine whether at least one characteristic of the at least one magnetomyogram exceeds a predetermined threshold; wherein the PPM has high sensitivity, high dynamic range, and high linearity that permit subtraction of environmental magnetic noise and resolution of small signals of interest. The PPM includes a pulsed polarization means, a probing means, a sensing volume, and a detector. The PPM is configured to operate in the range of 0.1 μT to 100 μT. The PPM has high sensitivity, high dynamic range, and high linearity that permit subtraction of environmental magnetic noise and resolution of small signals of interest. The torso and/or background field is reoriented to measure different components of the fields generated by the muscles.

PPM sensors can also perform all of these measurements in a magnetic shield as well. A simple 1- or 2-layer magnetic shield can be employed to reduce very large magnetic noise sources or to ensure a controlled environment. The shield must have a bias field applied inside. Unlike zero field magnetometers, the need to regulate or zero the magnetic field is dramatically reduced because the sensors work in a wide range of field values.

Figure 6:
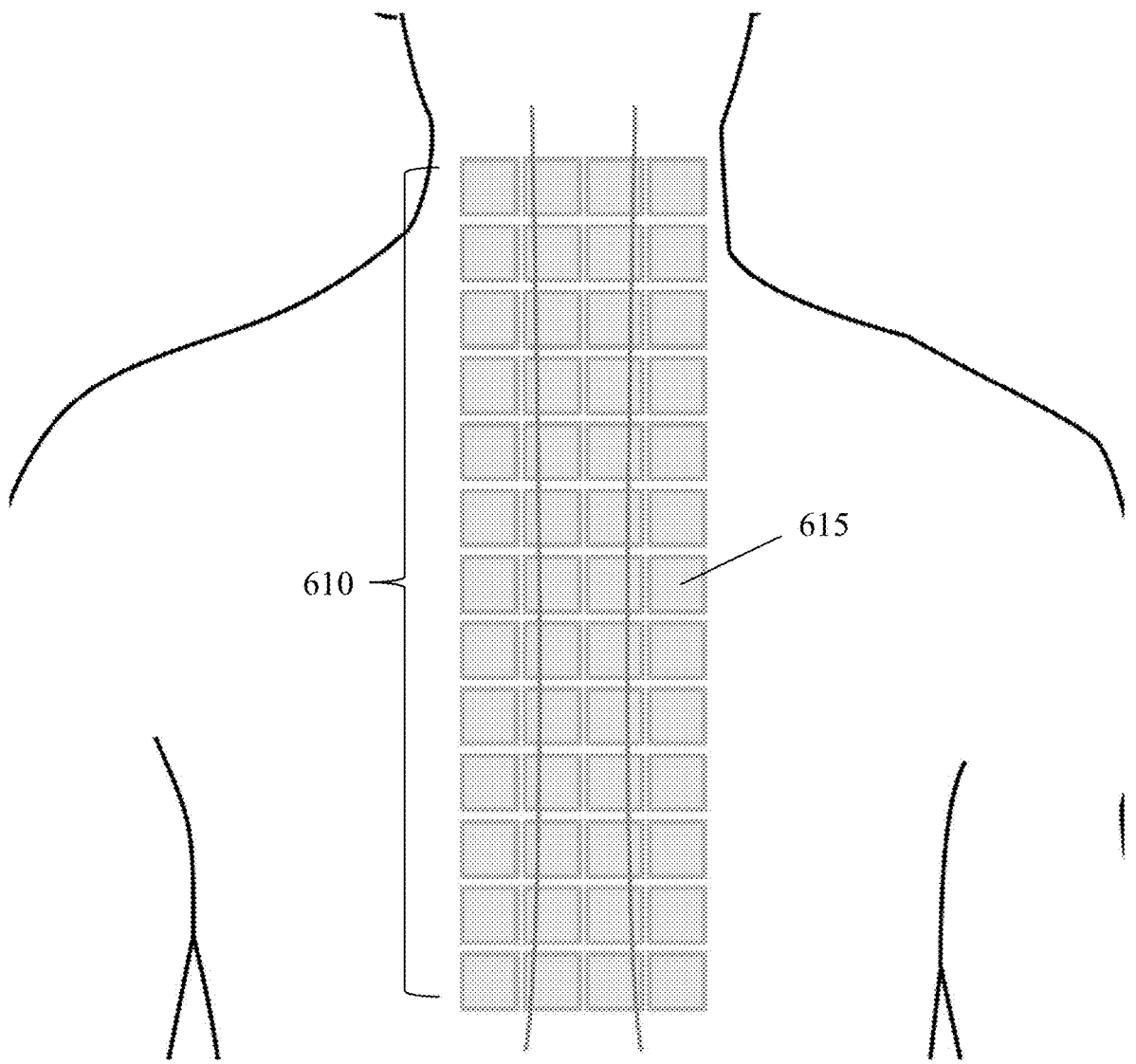
FIG. 6 shows an unshielded array of sensors arranged along the spine to perform magnetospinography according to one embodiment.

FIG. 6 shows an array of PPM sensors arranged along the spine to perform magnetospinography. In one embodiment, a magnetospinography device is used to make such measurement. The magnetospinography device includes: a vest configured to be worn over a part of the torso of a subject, the vest having an array 610 of PPM 615 configured to measure magnetic fields associated with sensory activities at corresponding locations of the cervical spinal cord and spinal nerve of the subject over a period of time; a control unit to operate the PPM sensors; and a processor configured to process the detected magnetic fields to generate at least one magnetospinogram, and determine whether at least one characteristic of the at least one magnetospinogram exceeds a predetermined threshold. The PPM has high sensitivity, high dynamic range, and high linearity that permit subtraction of environmental magnetic noise and resolution of small signals of interest. The PPM includes a pulsed polarization means, a probing means, a sensing volume, and a detector. The PPM is configured to operate in the range of 0.1 µT to 100 µT. The PPM has high sensitivity, high dynamic range, and high linearity that permit subtraction of environmental magnetic noise and resolution of small signals of interest.

Figure 7:
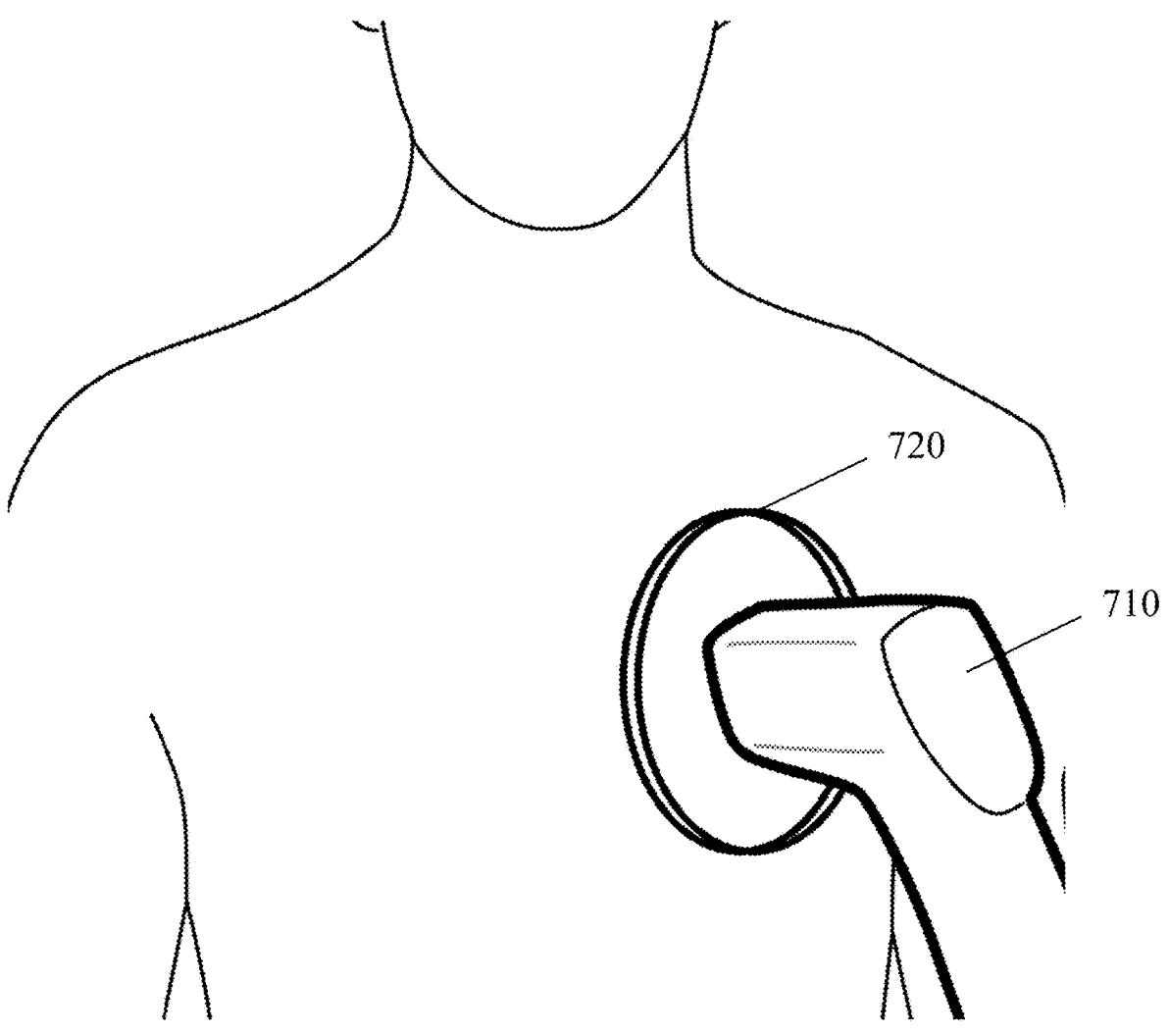
FIG. 7 shows an unshielded sensor array with nanoparticle polarization coil for magnetic relaxometry of magnetic nanoparticles according to one embodiment.

FIG. 7 shows a PPM sensor 710 with nanoparticle polarization coil 720 for magnetic relaxometry of magnetic nanoparticles. In one embodiment, a magnetorelaxometry imaging device is used to make such measurement. The magnetorelaxometry imaging device includes: a injection device for administering magnetic nanoparticles into a region of interest of a subject; a magnetic field generator configured to apply a magnetic field to the region of interest to magnetize the magnetic nanoparticles; an array of PPM configured to detect magnetization decay signals of the magnetic nanoparticle at corresponding locations after the magnetic field is off; a control unit to operate the PPM sensors; and a processor configured to process the detected to generate at least one image of the region of interest, and determine whether the at least one characteristic of the at least one image exceeds a predetermined threshold; wherein the PPM has high sensitivity, high dynamic range, and high linearity that permit subtraction of environmental magnetic noise and resolution of small signals of interest. The PPM includes a pulsed polarization means, a probing means, a sensing volume, and a detector. The PPM is configured to operate in the range of 0.1 µT to 100 µT. The PPM has high sensitivity, high dynamic range, and high linearity that permit subtraction of environmental magnetic noise and resolution of small signals of interest. The polarization coil used for nanoparticles and the polarization coil used to aid pumping in PPM are coordinated to maximize signal.

While the present disclosure describes at some length and with some particularity with respect to the several described embodiments, it is not intended that it should be limited to any such particulars or embodiments or any particular embodiment, but it is to be construed so as to provide the broadest possible interpretation in view of the related art and, therefore, to effectively encompass various embodiments herein. Furthermore, the foregoing describes various embodiments foreseen by the inventor for which an enabling description was available, notwithstanding that modifications of the disclosure, not presently foreseen, may nonetheless represent equivalents thereto.

What is claimed is:

1. A system for measuring biomagnetic signals of a biological subject in an unshielded measurement environment, comprising:

a pulsed pump magnetometer (PPM) configured to be arranged at a desired location over the biological subject;

at least one processor configured to:

operate the PPM to detect a biomagnetic signal from the biological subject over a period of time; and process the detected biomagnetic signal to generate a result indicative of a characteristic or condition associated with the biological subject;

wherein the PPM comprises:

at least one atomic vapor cell;

at least one pulsed pump laser and at least one probe laser which is pulsed or operated continuously; and a magnetic field coil configured to generate a pulsed magnetic field that has a component parallel to a pump axis of one of the at least one pulsed pump laser, the magnetic field coil being configured to be turned off faster than a Larmor precession period of a gas in one of the at least one atomic vapor cell.

2. The system of claim 1, wherein one or more of the PPM are arranged as an array in a device configured to fit on or near a head of the subject, the array is configured to detect neuromagnetic signals from the subject over the period of time.

3. The system of claim 2, wherein each of the one or more of the PPM measures a total magnetic field in a background magnetic field of greater magnitude than a brain-generated field, the PPM measurement being dominated by a projection of the brain-generated field onto the background magnetic field.

4. The system of claim 2, wherein the head and/or a background magnetic field is configured to be reoriented relative to the array to measure different components of neuromagnetic fields generated by a brain.

5. The system of claim 2, wherein the array is arranged as a set of paired PPMs, as two-point gradiometers, or as a set of multiple independent PPMs operated independently and the set of multiple independent PPMs being subject to post-processing as higher order multiple gradiometers.

6. The system of claim 1, wherein one or more of the PPM are arranged as an array in a vest or apparatus configured to be worn or placed over a part of a torso of the subject, the array is configured to measure gastric magnetic fields at corresponding locations of an organ inside the torso of the subject over the period of time.

7. The system of claim 1, wherein one or more of the PPM are arranged as an array in a vest or apparatus configured to be worn or placed over a part of a torso of the subject, the array is configured to measure neuromagnetic fields associated with sensory activities at corresponding locations of a cervical spinal cord and spinal nerve of the subject over the period of time.

8. The system of claim 1, wherein one or more of the PPM are arranged as an array in a vest or apparatus configured to be worn or placed over a part of an arm, leg or muscle of interest of the subject, the array is configured to measure magnetic fields associated with sensory activities at corresponding locations of muscles of the subject over the period of time.

9. The system of claim 1, further comprising:

an injection device for administering magnetic nanoparticles into a region of interest of the subject;

a magnetic field generator configured to apply a magnetic field to the region of interest to magnetize the magnetic nanoparticles;

wherein one or more of the PPM are arranged as an array configured to detect magnetization decay signals of the magnetic nanoparticles at corresponding locations after the magnetic field is off.

10. The system of claim 1, wherein the PPM comprises a controller configured to convert detected light signals from the PPM to total magnetic field measurements, and wherein the PPM is configured to operate in a range of background magnetic field strengths from less than 1 µT to more than 100 µT.

11. A method of measuring biomagnetic signals of a biological subject in an unshielded measurement environment using a pulsed pump magnetometer (PPM), comprising:

arranging one or more of the PPM at a desired location over a biological subject;

operating the one or more of the PPM to detect a biomagnetic signal from the biological subject over a period of time;

processing the detected biomagnetic signal to generate a result indicative of a characteristic or condition associated with the biological subject;

wherein each of the one or more of the PPM comprises:

at least one atomic vapor cell;

at least one pulsed pump laser and at least one probe laser which is pulsed or operated continuously; and a magnetic field coil configured to generate a pulsed magnetic field that has a component parallel to a pump axis of one of the at least one pulsed pump laser, the magnetic field coil being configured to be turned off faster than a Larmor precession period of a gas in one of the at least one atomic vapor cell.

12. The method of claim 11, further comprising:

arranging the one or more of the PPM as an array in a device configured to fit on or near a head of the subject, and configuring the array to detect neuromagnetic signals at corresponding locations of a brain of the subject over the period of time.

13. The method of claim 12, wherein each of the one or more of the PPM measures a total magnetic field in a background magnetic field of greater magnitude than a brain-generated field, the PPM measurement being dominated by a projection of the brain-generated field onto the background magnetic field.

14. The method of claim 12, further comprising reorienting the head and/or a background magnetic field relative to the array to measure different components of neuromagnetic fields generated by the brain.

15. The method of claim 12, further comprising arranging the array as a set of paired PPMs as two-point gradiometers, or as a set of multiple independent PPMs operated independently and the set of multiple independent PPMs being subject to post-processing as higher order multiple gradiometers.

16. The method of claim 12, wherein the magnetic field coil is configured to aid pumping in the one or more of the PPM to maximize the biomagnetic signal.

17. The method of claim 11, further comprising:

arranging the one or more of the PPM as an array in a vest or apparatus configured to be worn or placed over a torso of the subject, and configuring the array to measure gastric magnetic fields at corresponding locations of an organ inside the torso of the subject over the period of time.

18. The method of claim 11, further comprising:

arranging the one or more of the PPM as an array in a vest or apparatus configured to be worn or placed over a torso of the subject, and configuring the array to measure neuromagnetic magnetic fields associated with sensory activities at corresponding locations of a cervical spinal cord and spinal nerve of the subject over the period of time.

19. The method of claim 11, further comprising:

arranging the one or more of the PPM as an array in a vest or apparatus configured to be worn or placed over a part of an arm, leg or muscle of interest of the subject, and configuring the array to measure magnetic fields associated with sensory activities at corresponding locations of muscles of the subject over the period of time.

20. The method of claim 11, further comprising:

injecting magnetic nanoparticles into a region of interest of the subject;

applying a magnetic field to the region of interest to magnetize the magnetic nanoparticles;

arranging the one or more of the PPM as an array configured to detect magnetization decay signals of the magnetic nanoparticles at corresponding locations after the magnetic field is off.

* * * * *